(12) United States Patent
Müller et al.

(10) Patent No.: US 8,314,243 B2
(45) Date of Patent: Nov. 20, 2012

(54) PROCESS FOR CATALYTICALLY PREPARING AROMATIC OR HETEROAROMATIC NITRILES

(75) Inventors: Nikolaus Müller, Monheim (DE); Wolfgang Mägerlein, Mannheim (DE); Alain Cotté, Leverkusen (DE); Matthias Beller, Ostseebad Nienhagen (DE); Thomas Schareina, Cammin (DE); Alexander Zapf, Rosenheim (DE)

(73) Assignee: Saltigo GmbH, Langenfeld (DE)

( * ) Notice: Subject to any disclaimer, the term of this patent is extended or adjusted under 35 U.S.C. 154(b) by 685 days.

(21) Appl. No.: 11/986,398

(22) Filed: Nov. 21, 2007

(65) Prior Publication Data

US 2008/0194829 A1 Aug. 14, 2008

(30) Foreign Application Priority Data

Nov. 29, 2006 (DE) .......................... 10 2006 056 208

(51) Int. Cl.
*C07D 211/78* (2006.01)
*A01N 43/38* (2006.01)

(52) U.S. Cl. ....................................... 546/286; 514/411

(58) Field of Classification Search .................. 546/286; 558/411
See application file for complete search history.

(56) References Cited

OTHER PUBLICATIONS

Schareina et al Journal of Organometallic Chemistry 2004, 689, 4576-4583.*
Schareina, Thomas, et al.; "Potassium hexacyanoferrate(II)-a new cyanating agent for the palladium-catalyzed cyanation of aryl halides", Chemical Communications; 2004, pp. 1388-1389.
Cheng Y-N, et al.; "Cyanation of aryl chlorides with potassium hexacyanoferrate(II) catalyzed by cyclopalladated ferrocenylimine tricyclohexylphosphine complexes", Synlett, 2007, pp. 543-546.
Schareina, et al.; "A new palladium catalyst system for the cyanation of aryl chlorides with K4[Fe(CN)6]", Tetrahedron Letters, 2007, pp. 1087-1090.
Bedford R. B., et al.; "The development of palladium catalysts for CC and Cheteroatom bond forming reactions of aryl chloride substrates", Coordination Chemistry Reviews, 2004, pp. 2283-2321.

\* cited by examiner

*Primary Examiner* — Janet Andres
*Assistant Examiner* — John Mabry
(74) *Attorney, Agent, or Firm* — Michael A. Miller

(57) ABSTRACT

A process is described for catalytically preparing optionally substituted aromatic or heteroaromatic nitrites of the general formula (I)

$$Ar-CN \qquad (I)$$

by reacting the corresponding aryl halides of the general formula (II)

$$Ar-X \qquad (II)$$

in which
X is chlorine, bromine, iodine, triflate, nonaflate, mesylate or tosylate and
Ar is an optionally substituted aromatic or heteroaromatic radical,
characterized in that the reaction is performed in the presence of a palladium compound, a phosphine of the general formula (III) or (IV)

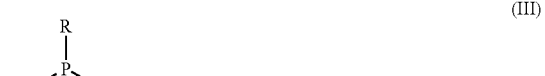

(III)

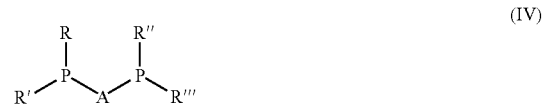

(IV)

where
R is an alkyl radical and
R', R" and R'" are each an alkyl radical or an aryl radical or heteroaryl radical and
A is an alkylene or arylene radical, and potassium hexacyanoferrate(II) or potassium hexacyanoferrate(III), optionally in a solvent and optionally with addition of a base.

6 Claims, No Drawings

PROCESS FOR CATALYTICALLY PREPARING AROMATIC OR HETEROAROMATIC NITRILES

The present invention relates to a process for preparing optionally substituted aromatic or heteroaromatic nitriles by cyanating the corresponding aryl halides with catalysts based on palladium complexes using potassium hexacyanoferrate (II) or potassium hexacyanoferrate(III) as the cyanide source.

Aromatic or heteroaromatic nitriles have industrial significance as starting materials for fine chemicals, agrochemical products and pharmaceutical intermediates. An industrially employed method for preparing aromatic nitriles is the ammonoxidation of substituted toluenes. This process is of industrial interest only when the corresponding toluenes are available inexpensively. Furthermore, the ammonoxidation does not succeed in the presence of oxidation-sensitive substituents in the substrate. Further industrial processes for preparing benzonitriles are reactions of carboxylic acids and ammonium salts or amides by distillation with strongly water-binding substances (e.g. $P_2O_5$) and reaction of carboxylic acids or esters in the vapour phase with ammonia over an Al fixed bed at 500° C.

Inexpensive starting materials for aromatic nitriles are the corresponding chlorobenzenes and in some cases the corresponding bromobenzenes. However, the substitution of chlorine with cyanide by known processes often succeeds only unsatisfactorily. For example, aromatic halides react with HCN in the vapour phase at 650° C. or at 480-650° C. in the presence of a metal catalyst or metal oxide catalyst. Catalysts which accelerate the reaction of aryl halides with cyanide under relatively mild reaction conditions are palladium complexes and nickel complexes. For instance, R. Breitschuh, B. Pugin, A. Idolese and V. Gisin (EP-A 0 787 124 B1 and U.S. Pat. No. 5,883,283) describe the preparation of substituted 3-aminobenzonitriles from the corresponding substituted 3-aminochlorobenzenes in the presence of preferably Ni complexes and stoichiometric amounts of a complexing substance. A disadvantage in this process is the use of an excess of reducing agent and the restriction of the reaction to a specific substrate class.

B. R. Cotter (U.S. Pat. No. 4,211,721) describes the positive influence of ether components from the group of 18-crown-6, polyethers, alkoxy polyethers or mixtures thereof having a molar mass of 200-25 000 as a cocatalyst on the palladium-catalysed cyanation of aryl halides. In the examples of the application mentioned, however, it becomes clear that only activated (electron-poor) chloroaromatics such as 4-chlorobenzotrifluoride react under the inventive reaction conditions, the product yields of the corresponding benzonitriles being only approx. 45%. Non-activated chloroaromatics such as chlorotoluene give rise to the target product in only 5 to 11% yields. Such yields make industrial implementation of the process economically impossible.

J. B. Davison, R. J. Jasinski and P. J. Peerce-Landers (U.S. Pat. No. 4,499,025) describe the preparation of aromatic nitriles from chloroaromatics, catalysed by a group VIII metal (0) complex which is formed electrochemically. However, this procedure is exceptionally expensive compared to conventional batch processes. Furthermore, there is no example of a successful conversion of a chloroaromatic in good yields.

A. Viauvy and M. Casado (EP-A 0 994 099 A1) further describe the reaction of chloroaromatics to give the corresponding nitrile with copper cyanide and a bromide source, or alkali metal cyanide or tetraalkylammoniumcyanide in the presence of copper bromide and a phase transfer catalyst or copper cyanide and lithium iodide. These procedures have the disadvantage that superstoichiometric amounts of heavy metal salt wastes are formed. Furthermore, the yields of benzonitriles from chloroaromatics are not satisfactory.

M.-H. Rock and A. Merhold (DE-A 197 06 648 A1 and WO 98/37 058) describe the preparation of aromatic nitriles from chloroaromatics in the presence of a nickel catalyst and of a ketone by reaction with cyanides. However, the reaction can be performed successfully only when the cyanide concentration is strictly controlled, since the catalyst is otherwise cyanated irreversibly. A disadvantage in this process is again the need to use a reducing agent such as zinc, which leads to additional heavy metal salt wastes, and the use of specific ketones as solvents.

R. K. Arvela and N. E. Leadbeater describe the cyanation of chloroaromatics in the presence of stoichiometric amounts of nickel(II) bromide and sodium cyanide (J. Org. Chem. 2003, 68, 9122-5). In addition to the amount of nickel salt wastes resulting therefrom, the use of microwave radiation for energy introduction is disadvantageous for industrial reactions.

H. R. Chobanian, B. P. Fors and L. S. Lin describe the reaction of chloroaromatics with zinc(II) cyanide using a Pd catalyst with S-Phos as a ligand (Tetrahedron Lett. 2006, 47, 3303-5). A disadvantage here too is the generation of stoichiometric amounts of heavy metal salt wastes and the use of an expensive phosphine ligand in high concentration (2-10 mol % based on the chloroaromatic).

Beller and coworkers describe the influence of crown ethers, diphosphine ligands and diamine ligands on the palladium-catalysed reaction of aryl halides with alkali metal cyanides (DE-A 101 13 976, Tetrahedron Lett. 2001, 42, 6707-10). Based on these studies, the metered addition of acetone cyanohydrin as a cyanide donor was tested in the system described (Angew. Chem. 2003, 115, 1700-3). Moreover, the metering of TMSCN (J. Organomet. Chem. 2003, 684, 50-5) or hydrocyanic acid (DE-A 103 23 574) was described.

All above-described processes for cyanating aryl halides or heteroaryl halides have the disadvantage that they use cyanide sources in which free cyanide is present in excess, so that the cyanide ligand, owing to its strongly complexing action, can block the Pd catalyst. Therefore, these processes generally have the disadvantage that the cyanide source has to be metered in in a controlled manner and/or that often poor catalyst activities and productivities are observed. In addition, these cyanide sources are highly toxic and can easily release hydrocyanic acid, so that their industrial use is possible only with particular safety measures.

These disadvantages have been bypassed by Beller et al. by using potassium hexacyanoferrate(II) $K_4[Fe(CN)_6]$ as a nontoxic and easy-to-handle cyanide source. This cyanating reagent is of low toxicity, dissolves in water without decomposition and is even used in the food and drink industry, for example in the production of table salt or for preserving wines (Roempp Lexikon Chemie, Georg Thieme Verlag, Stuttgart/N.Y., 1999). Chem. Commun. 2004, 1388-1389 describes a Pd-catalysed process for cyanation using potassium hexacyanoferrate (II). Applications DE-A 10 2005 009 517.8 and DE-A 10 2006 042439.5 describe Cu-catalysed processes for cyanation using potassium hexacyanoferrate(II) $K_4[Fe(CN)_6]$, or potassium hexacyanoferrate(III) $K_3[Fe(CN)_6]$. However, a disadvantage is that these processes can efficiently convert only aryl bromides and heteroaryl bromides. For industrial applications, however, aryl chlorides and heteroaryl chlorides are significantly more attractive, since they are generally available and obtainable less expensively and more widely than other aryl halides, heteroaryl halides, aryl pseudohalides or heteroaryl pseudohalides. However, with the processes known to date from the prior art which use potassium hexacyanoferrates for cyanation, a reaction of the aryl chlorides or heteroaryl chlorides, which are less reactive compared to aryl bromides or heteroaryl bromides, is possible only with very low yields, if at all. This is especially true of unactivated or deactivated (electron-rich) and sterically hindered aryl chlorides or heteroaryl chlorides. The sole example of a successful reaction which has been described is the above-cited Chem. Commun. publication, the Pd-catalysed cyanation of the strongly activated 4-chloroquinoline using potassium hexacyanoferrate(II).

It was thus an object of the present invention to develop a process for cyanating aryl halides and heteroaryl halides with potassium hexacyanoferrate, which is notable compared to the prior art especially for a greater substrate range, especially in relation to an efficient reaction of both activated and deactivated aryl chlorides and heteroaryl chlorides. Equally, the process according to the invention should be readily usable on the industrial scale and be superior to the prior art processes in relation to catalyst productivity and hence also in relation to economic points of view.

The stated object has been achieved by, in the process according to the invention, performing the catalytic preparation of optionally substituted aromatic or heteroaromatic nitriles of the general formula (I)

by reacting the corresponding aryl halides of the general formula (II)

in which

X is chlorine, bromine, iodine, triflate (trifluoromethanesulfonate), nonaflate, (nonafluorobutanesulfonate), mesylate or tosylate, preferably chlorine and bromine, more preferably chlorine, and Ar is an optionally substituted aromatic or heteroaromatic radical, preferably an optionally substituted aromatic radical, using potassium hexacyanoferrate(II) and/or potassium hexacyanoferrate(III), optionally in the presence of a base and in the presence of a Pd compound and of a phosphorus ligand of the formula (III) or (IV), where R is a cyclic or acyclic, branched or unbranched alkyl group and R', R" and R'" are either an alkyl group as defined above or an optionally substituted aryl or heteroaryl group, and A is an optionally substituted alkylene or arylene unit. The R, R' and R" radicals are preferably each an alkyl group having 1 to 10 carbon atoms and A is an alkylene unit having 1 to 10 carbon atoms

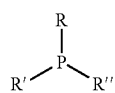

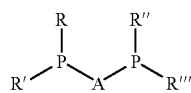

The palladium compounds used may be known Pd(0) and Pd(II) compounds. Typical examples are salts, for example PdCl$_2$ and Pd(OAc)$_2$, and also Pd complexes, for example Pd(PPh$_3$)$_4$, Pd(dba)$_2$, PdCl$_2$(PhCN)$_2$, allylpalladium chloride dimer, and also complexes of palladium(0) or (II) with the abovementioned ligands of the formulae (III) and (IV). Preference is given to Pd(dba)$_2$ and Pd(OAc)$_2$.

The palladium compound used should be present in the reaction mixture in sufficient amount. The person skilled in the art will select the necessary use amount with reference to economic considerations (rapidity of the reaction, yield, material costs). In the process according to the invention, turnover values of the catalysts in the order of magnitude of at least 10 to 100 000 can be realized. It is advantageous to use the palladium compound in an amount of 0.001 to 10 mol % based on the aryl halide or heteroaryl halide; preference is given to using amounts of 0.01 mol % to 2 mol %.

The phosphine ligand used may be a monodentate phosphine of the formula (III) or a bidentate phosphine of the formula (IV). The phosphines may be used as such or in the form of phosphonium salts, for example acid adducts, for example PR$_3$.HX (where HX is a Bronsted acid), in which case a simultaneously present base in the reaction mixture ensures the in situ release of the phosphine. Preference is given to using phosphines of the formula (III) where R and R' are each an alkyl radical with the definition described in detail below and R" is an aryl radical with the definition described in detail below. Particular preference is given to the use of n-butylbis(adamantyl)phosphine, tri(tert-butyl)phosphine, tricyclohexylphosphine, phenyldi(tert-butyl)phosphine, 2-dicyclohexylphosphino-1-phenylpyrrole, 2-dicyclohexylphosphino-1-(2',4',6'-trimethylphenyl)imidazole, 2-(di-tert-butylphosphino)-1-(2',4',6'-trimethylphenyl)imidazole, 2-(di-tert-butylphosphino)-1-(2'-trimethylsilylphenyl)pyrrole and 2-dialkylphosphino-2'-dialkylaminobiphenylene. Very particular preference is given to the use of n-butylbis(adamantyl)phosphine and tri(tert-butyl)phosphine.

With regard to the amount of the phosphine ligand used, it is possible in the process according to the invention to use molar palladium:phosphine ligand ratios of 1:100 up to 10:1. Preference is given to using molar palladium:phosphine ligand ratios of 1:10 to 2:1; particular preference is given to molar ratios of 1:5 to 1:1.

Phosphine ligand and palladium may be added together as a complex or individually.

The solvents used in the process according to the invention are generally inert organic solvents and/or water. Preference is given to dipolar aprotic solvents, for example aliphatic esters or amides and mixtures thereof. Particular preference is given to the use of N,N-dimethylacetamide and N-methylpyrrolidin-2-one. The reactions may also be performed in bulk, i.e. without solvent.

In some cases, the addition of bases may be advantageous in the process according to the invention. In this case, either organic or inorganic bases may be used. Examples are amines, carboxylates, carbonates, hydrogen carbonates, phosphates, alkoxides and hydroxides. Preference is given to using alkali metal acetates, carbonates and hydroxides, and alkaline earth metal acetates, carbonates and hydroxides. Particular preference is given to the addition of alkali metal carbonates, such as sodium carbonate or potassium carbonate.

The bases used are used preferably in amounts of 1-100 mol % based on the aryl halide or heteroaryl halide. Particular preference is given to amounts of 10-50 mol % of the base.

The cyanide source used in the process according to the invention may be potassium hexacyanoferrate(II) and potassium hexacyanoferrate(III). Preference is given to the use of potassium hexacyanoferrate(II). Since all six cyanide ligands are available for reaction in the process according to the invention, use of the cyanide source in an amount of 16.7 mol % or in a higher amount is advantageous. The person skilled in the art will select the necessary use amount of the cyanide source on the basis of economic considerations (rapidity of the reaction, yield, material costs). Preference is given to the use of 15 mol % to 50 mol %, particular preference to the use of 16 to 25 mol %, of the cyanide source, based on the aryl halide or heteroaryl halide.

The reaction is performed at temperatures of 20 to 220° C. Preference is given to reaction temperatures of 80 to 200° C.; particular preference is given to working at 100 to 180° C.

The reaction is normally performed at ambient pressure. However, it can also be performed without any problems under pressure, for example in an autoclave or pressure tube.

It is possible with the potassium hexacyanoferrate(II) cyanide source used in the process according to the invention and the corresponding catalyst system, for example composed of a combination of a palladium compound, of a phosphine ligand and optionally of a base, to realize significantly better results in cyanations of aryl halides and heteroaryl halides than with commonly known reaction systems. Compared to the prior art, it can be seen as a significant advance that the process according to the invention enables, using the safe and inexpensive potassium hexacyanoferrates as the cyanide source, the cyanation even of the relatively unreactive but very inexpensive and widely available chloroaromatics.

In principle, there is no restriction with regard to the use of aromatics or heteroaromatics. In particular, the Ar radical may be a ($C_6$-$C_{19}$)-aryl radical or a ($C_3$-$C_{18}$)-heteroaryl radical with 1, 2 or 3 heteroatoms such as nitrogen, oxygen or sulphur in the ring.

It is possible that the Ar radical may bear up to eight substituents, which may each independently be ($C_1$-$C_8$)-alkyl, ($C_3$-$C_8$)-cycloalkyl, ($C_2$-$C_8$)-alkenyl, ($C_2$-$C_8$)-alkynyl, ($C_7$-$C_{20}$)-aralkyl radical, OH, O—[($C_1$-$C_8$)-alkyl], OC(O)—[($C_1$-$C_8$)-alkyl], O-phenyl, phenyl, $NH_2$, $NO_2$, NO, N[($C_1$-$C_8$)-alkyl]$_2$, NH[($C_1$-$C_8$)-alkyl], NHC(O)—[($C_1$-$C_8$)-alkyl], N[($C_1$-$C_8$)-alkyl]C(O)—[($C_1$-$C_8$)-alkyl], SH, S-phenyl, S—[($C_1$-$C_8$)-alkyl], fluorine, chlorine, $CF_3$, CN, COOH, COO—[($C_1$-$C_8$)-alkyl], CONH—[($C_1$-$C_8$)-alkyl], COO-phenyl, CONH-phenyl, CHO, $SO_2$—($C_1$-$C_8$)-alkyl, SO—($C_1$-$C_8$)-alkyl, PO-(phenyl)$_2$, PO—[($C_1$-$C_8$)-alkyl]$_2$, $PO_3H_2$, PO[O—($C_1$-$C_8$)-alkyl]$_2$, $SO_3H$, $SO_3M$, $SO_3$—[($C_1$-$C_8$)-alkyl], Si[($C_1$-$C_8$)-alkyl]$_3$, ($C_1$-$C_8$)-haloalkyl and ($C_1$-$C_8$)-acyl.

($C_1$-$C_8$)-Alkyl is considered to be methyl, ethyl, n-propyl, isopropyl, n-butyl, isobutyl, sec-butyl, tert-butyl, pentyl, hexyl, heptyl or octyl, including all bonding isomers. These may be mono- or polysubstituted by ($C_1$-$C_8$)-alkoxy, ($C_1$-$C_8$)-haloalkyl, OH, halogen, $NH_2$, $NO_2$, SH, S—($C_1$-$C_8$)-alkyl.

($C_2$-$C_8$)-Alkenyl is understood to mean, with the exception of methyl, a ($C_1$-$C_8$)-alkyl radical as listed above which has at least one double bond.

($C_2$-$C_8$)-Alkynyl is understood to mean, with the exception of methyl, a ($C_1$-$C_8$)-alkyl radical as listed above which has at least one triple bond.

($C_1$-$C_8$)-Acyl is understood to mean a ($C_1$-$C_8$)-alkyl radical which is bonded to the molecule via a —C=O function.

($C_3$-$C_8$)-Cycloalkyl is understood to mean cyclopropyl, cyclobutyl, cyclopentyl, cyclohexyl or cycloheptyl radicals, etc. These may be substituted by one or more halogens and/or N—, O—, P—, S-containing radicals and/or have N, O, P, S atoms in the ring, for example 1-, 2-, 3-, 4-piperidyl, 1-, 2-, 3-pyrrolidinyl, 2-, 3-tetrahydrofuryl, 2-, 3-, 4-morpholinyl. This may be mono- or polysubstituted by ($C_1$-$C_8$)-alkoxy, ($C_1$-$C_8$)-haloalkyl, OH, halogen, $NH_2$, $NO_2$, SH, S—($C_1$-$C_8$)-alkyl, ($C_1$-$C_8$)-acyl, ($C_1$-$C_8$)-alkyl.

A ($C_6$-$C_{19}$)-aryl radical is understood to mean an aromatic radical having 6 to 18 carbon atoms. In particular, these include compounds such as phenyl, naphthyl, anthryl, phenanthryl, biphenyl radicals. This may be mono- or polysubstituted by ($C_1$-$C_8$)-alkoxy, ($C_1$-$C_8$)-haloalkyl, OH, halogen, $NH_2$, $NO_2$, SH, S—($C_1$-$C_8$)-alkyl, ($C_1$-$C_8$)-acyl, ($C_1$-$C_8$)-alkyl.

A ($C_7$-$C_{20}$)-aralkyl radical is a ($C_6$-$C_{19}$)-aryl radical which is bonded to the molecule via a ($C_1$-$C_8$)-alkyl radical.

($C_1$-$C_8$)-Alkoxy is a ($C_1$-$C_8$)-alkyl radical bonded to the molecule in question via an oxygen atom.

($C_1$-$C_8$)-Haloalkyl is a ($C_1$-$C_8$)-alkyl radical substituted by one or more halogen atoms.

In the context of the invention, a ($C_3$-$C_{18}$)-heteroaryl radical denotes a five-, six- or seven-membered aromatic ring system which is composed of 3 to 18 carbon atoms and has 1, 2 or 3 heteroatoms, for example nitrogen, oxygen or sulphur, in the ring. Such heteroaromatics are considered in particular to be radicals such as 1-, 2-, 3-furyl, 1-, 2-, 3-pyrrolyl, 1-, 2-, 3-thienyl, 2-, 3-, 4-pyridyl, 2-, 3-, 4-, 5-, 6-, 7-indolyl, 3-, 4-, 5-pyrazolyl, 2-, 4-, 5-imidazolyl, acridinyl, quinolinyl, phenanthridinyl, 2-, 4-, 5-, 6-pyrimidinyl. A ($C_4$-$C_{19}$)-heteroaralkyl is understood to mean a heteroaromatic system corresponding to the ($C_7$-$C_{20}$)-aralkyl radical.

Possible halogens are fluorine, chlorine, bromine and iodine.

EXAMPLES

General procedure for the examples which follow:

0.4 mmol of sodium carbonate, 0.4 mmol of potassium hexacyanoferrate(II), a suitable amount of palladium acetate and ligand were, as specified in the table, suspended in a pressure tube under argon in 2 ml of dry NMP. 2 mmol of haloaromatic and 200 ml of hexadecane as the internal standard for the GC analysis were added. The pressure tube was closed and heated to the temperature specified for 16 h. After cooling to room temperature, the mixture was diluted with 2 ml of water and 2 ml of ether. A sample of the organic phase was analysed by gas chromatography. To isolate the product, the aqueous phase was extracted with ether. The combined organic phases were washed with water and saturated NaCl solution and finally dried over sodium sulphate. After the solvent had been drawn off, the crude product was purified by column chromatography using silica gel or by distillation.

| No. | ArX | Pd(OAc)$_2$ [mol %] | Ligand (mol %) | Temp. [° C.] | Yield [%] | TON |
|---|---|---|---|---|---|---|
| 1 | Chlorobenzene | 0.1 | BuPAd$_2$(0.3) | 140 | 100 | 1000 |
| 2 | Chlorobenzene | 0.1 | PtBu$_3$(0.3) | 140 | 88 | 880 |
| 3 | 2-Chlorotoluene | 0.1 | BuPAd$_2$(0.3) | 160 | 90 | 900 |
| 4 | 4-Chlorotoluene | 0.2 | BuPAd$_2$(0.6) | 160 | 80 | 400 |
| 5 | 2-Chloro-m-xylene | 0.5 | BuPAd$_2$(1) | 140 | 69 | 138 |
| 6 | 3-Chloropyridine | 0.25 | BuPAd$_2$(1) | 160 | 95 | 380 |
| 7 | Bromobenzene | 0.05 | BuPAd$_2$(0.2) | 140 | 100 | 2000 |

-continued

| No. | ArX | Pd(OAc)$_2$ [mol %] | Ligand (mol %) | Temp. [° C.] | Yield [%] | TON |
|---|---|---|---|---|---|---|
| 8 | 2-Bromotoluene | 0.05 | BuPAd$_2$(0.2) | 140 | 100 | 2000 |
| 9 | 1-Bromonaphthalene | 0.05 | BuPAd$_2$(0.2) | 140 | 100 | 2000 |

The invention claimed is:

1. Process for catalytically preparing optionally substituted aromatic or heteroaromatic nitriles of the general formula (I)

Ar—CN  (I)

by reacting the corresponding aryl halides of the general formula (II)

Ar—X  (II)

in which

X is chlorine, bromine, iodine, triflate, nonaflate, mesylate or tosylate and

Ar is a phenyl and naphthyl optionally substituted with unsubstituted alkyl and halogen, characterized in that the reaction is performed in the presence of a palladium compound, a phosphine comprising n-butyl bis(adamantly)phosphine or tri(tert-butyl)phosphine, and potassium hexacyanoferrate(II), optionally in a solvent and optionally with addition of a base.

2. The process according to claim 1, characterized in that the palladium compounds used are known palladium(0) complexes or palladium(II) salts or complexes.

3. The process according to claim 1 or 2, characterized in that the palladium compounds used are palladium halides and complexes thereof, palladiumacetate, palladium-dibenzylideneacetone complexes or allylpalladium chloride dimer.

4. The process according to claim 1 characterized in that the palladium compound is used in an amount of 0.001 mol % to 10 mol % based on the aryl halide Ar—X used.

5. The process according to claim 1, characterized in that the reaction is effected at temperatures of 20 to 220° C.

6. The process according to claim 1, characterized in that the reaction is performed at ambient pressure.

* * * * *